United States Patent
Gobber et al.

(10) Patent No.: US 12,022,818 B2
(45) Date of Patent: Jul. 2, 2024

(54) BRACELET FOR THE DIFFUSION OF VOLATILE SUBSTANCES

(71) Applicant: Zobele Holding SPA, Trento (IT)

(72) Inventors: Cedric Gobber, Barcelona (ES); Moisés Caballero Tapia, Barcelona (ES); Jorge Alejandro Martinez Uribe, Barcelona (ES)

(73) Assignee: ZOBELE HOLDING SPA, Trento (IT)

( * ) Notice: Subject to any disclaimer, the term of this patent is extended or adjusted under 35 U.S.C. 154(b) by 402 days.

(21) Appl. No.: 16/758,342

(22) PCT Filed: Oct. 30, 2018

(86) PCT No.: PCT/EP2018/079666
§ 371 (c)(1),
(2) Date: Apr. 22, 2020

(87) PCT Pub. No.: WO2019/086428
PCT Pub. Date: May 9, 2019

(65) Prior Publication Data
US 2020/0337295 A1     Oct. 29, 2020

(30) Foreign Application Priority Data

Oct. 31, 2017  (ES) ............................... ES201731275

(51) Int. Cl.
| | |
|---|---|
| *A01M 1/20* | (2006.01) |
| *A01M 29/12* | (2011.01) |
| *A45D 34/00* | (2006.01) |
| *A61L 9/04* | (2006.01) |
| *A61L 9/12* | (2006.01) |

(52) U.S. Cl.
CPC .......... *A01M 1/2055* (2013.01); *A01M 29/12* (2013.01); *A45D 34/00* (2013.01); *A61L 9/042* (2013.01); *A61L 9/12* (2013.01); *A61L 2209/133* (2013.01)

(58) Field of Classification Search
None
See application file for complete search history.

(56) References Cited

U.S. PATENT DOCUMENTS

| | | | | |
|---|---|---|---|---|
| 4,058,972 | A * | 11/1977 | Weick | A44C 15/002 368/278 |
| 6,244,518 | B1 | 6/2001 | Pogue | |
| 2004/0206832 | A1 * | 10/2004 | Yeung | A61L 9/12 239/44 |
| 2006/0126444 | A1 * | 6/2006 | Ellner | A45F 5/00 368/246 |

FOREIGN PATENT DOCUMENTS

| | | |
|---|---|---|
| ES | 1078452 | 1/2013 |
| WO | WO2015010801 | 1/2015 |
| WO | WO2019086428 | 5/2019 |

OTHER PUBLICATIONS

English Machine Translation ES1078452 (U) obtained Jun. 27, 2022 at: https://worldwide.espacenet.com/publicationDetails/biblio?CC=ES&NR=1078452U&KC=U&FT=D&ND=3&date=20130124&DB=EPODOC&locale=en_EP# (Year: 2013).*
International Search Report dated Feb. 25, 2019 for PCT Application No. PCT/EP2018/079666.

* cited by examiner

*Primary Examiner* — Jessica Whiteley
(74) *Attorney, Agent, or Firm* — Sandberg Phoenix & von Gontard, P.C.

(57) ABSTRACT

The present invention relates to a bracelet for the diffusion of volatile substances, comprising a strap (1) and a refill (2) impregnated with volatile substances, and is characterized in that the refill (2) comprises an outer surface (21) provided with at least one rib (3), defining at least one evaporation chamber (4).

The present invention provides a bracelet for the diffusion of volatile substances having a higher volatile substance evaporation rate, with the refill having a size that is suitable for use in a bracelet and being firmly secured on the strap, even in bracelets for children.

20 Claims, 2 Drawing Sheets

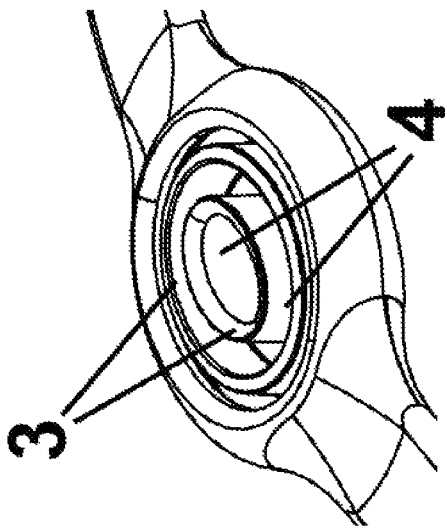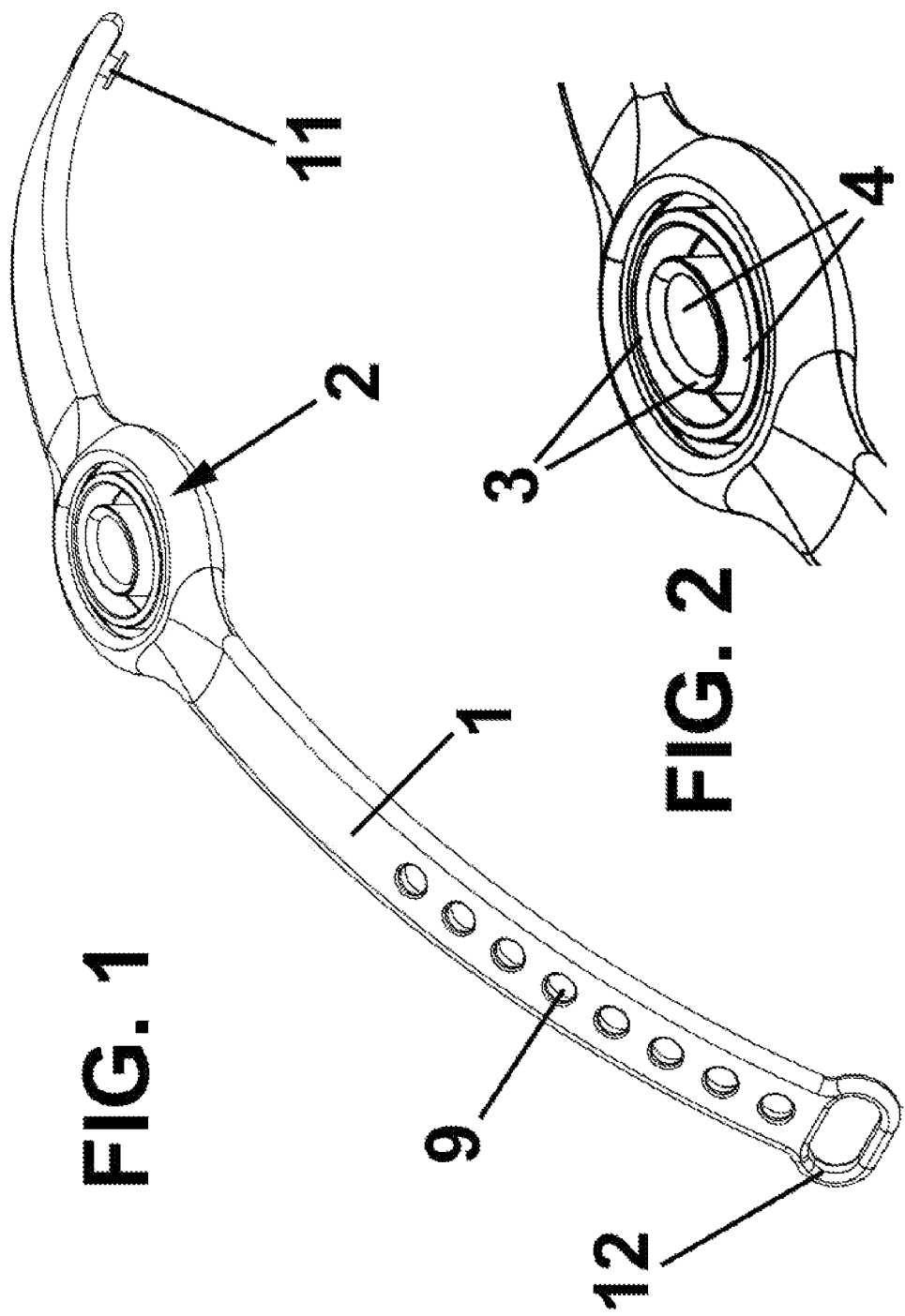

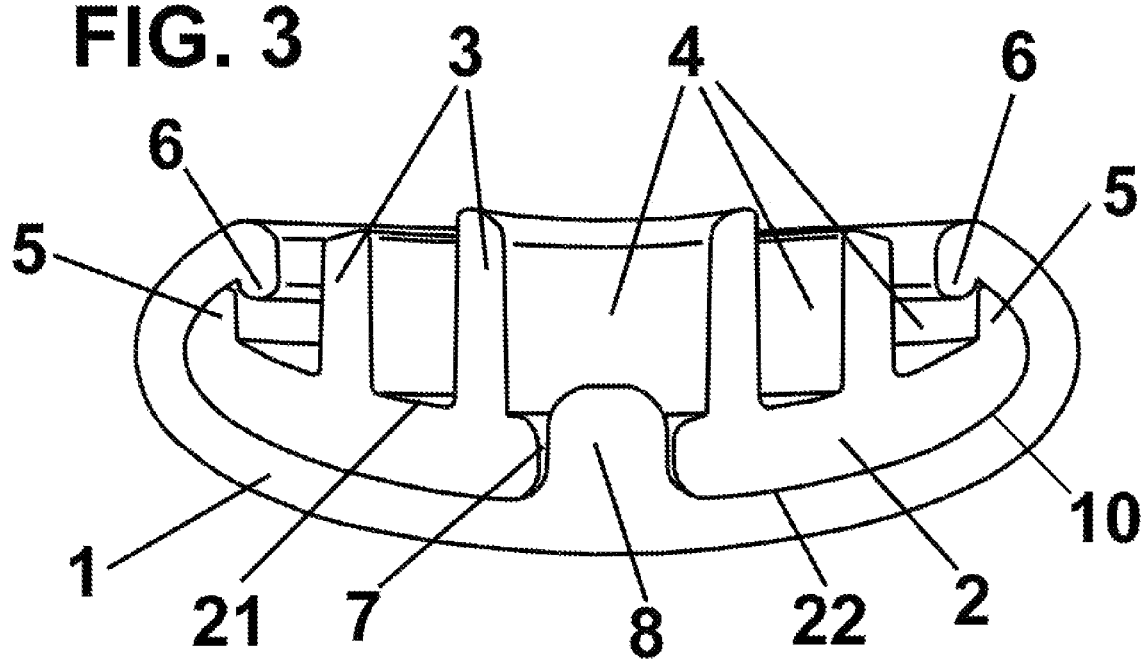

BRACELET FOR THE DIFFUSION OF VOLATILE SUBSTANCES

The present invention relates to a bracelet for the diffusion of volatile substances comprising a strap and a refill, providing an improved volatile substance evaporation rate.

BACKGROUND OF THE INVENTION

The use of volatile substance-diffusing bracelets to provide perfume or aromas or to repel insects, for example, is known.

Single-use diffusing bracelets which have said volatile substances that gradually diffuse over time impregnated therein and are disposed of and replaced with other ones once the volatile substances have been completely diffused are available today.

Diffusing bracelets comprising a strap and a refill are also known, being impregnated with volatile substances, such that when the refill is used up, it is replaced with another one using the same strap. These refills are usually plastic parts or membranes.

The main drawback of these refills used today in diffusing bracelets is their short service life, their surface that is exposed to limited evaporation, and their low volatile substance evaporation rate.

Refills having better evaporation rate, but also the drawback of being extremely bulky and difficult to secure on straps, particularly on straps for children, are also available today.

Therefore, an objective of the present invention is to provide a bracelet for the diffusion of volatile substances having a higher volatile substance evaporation rate, with the refill having a size being suitable for use in a bracelet and being firmly secured on the strap, even in bracelets for children.

DESCRIPTION OF THE INVENTION

The mentioned drawbacks are solved with the bracelet of the invention, while it also has other advantages that will be described below.

The bracelet for the diffusion of volatile substances such as, but not limited to, perfumes and insecticides, according to the present invention comprises a strap and a refill impregnated with volatile substances, and is characterized in that the refill comprises an outer surface provided with at least one rib, defining at least one evaporation chamber.

As a result of this feature, the evaporation capacity of the refill is increased by increasing the evaporation surface, without increasing the size of said refill.

According to a preferred embodiment, the outer surface of the refill comprises at least two ribs, defining at least two concentric evaporation chambers.

Said rib(s) preferably define a circular or oval shape, although they may have any suitable shape, for example, a square or rectangular shape.

Advantageously, the outer surface of the refill also comprises a perimetral rim or perimeter rim for the detachable fixing of the refill to the strap, and the strap comprises a flange contacting the perimetral rim or perimeter rim for detachably fixing the refill to the strap.

Furthermore, the refill also comprises a preferably substantially smooth inner surface which, in its usage position, is in contact with the strap or with the user.

To improve the detachable fixing of the refill, the refill also comprises a securing hole which houses therein a protrusion of the strap in the usage position of the refill.

Said refill is preferably made of a plastic material, for example, ethylene-vinyl acetate (EVA), although it can be made of any material which can be impregnated with the volatile substance and to which the shape described above can be imparted.

Advantageously, said refill is detachably housed inside a housing of the strap, being fixed therein by means of the contact between the flange and the perimetral rim or perimeter rim.

BRIEF DESCRIPTION OF THE DRAWINGS

To better understand what has been set forth, drawings in which a practical embodiment is schematically shown only by way of non-limiting example are attached.

FIG. 1 is a perspective view of the bracelet for the diffusion of volatile substances according to the present invention;

FIG. 2 is a perspective view of the refill mounted in its usage position on the strap of the bracelet for the diffusion of volatile substances according to the present invention; and FIG. 3 is a section view of the refill mounted in its usage position on the strap of the bracelet for the diffusion of volatile substances according to the present invention.

DESCRIPTION OF A PREFERRED EMBODIMENT

As shown in FIG. 1, the bracelet for the diffusion of volatile substances according to the present invention comprises a strap 1 and a refill 2 which is impregnated with volatile substances and replaced when it is used up.

The strap 1 is of a conventional type, for example, one that is made of an elastomeric-type plastic material, such as silicone. For the placement thereof on a user's wrist, the strap 1 comprises a eyelet 12 arranged at one end of the strap 1, into which there is introduced the opposite end of the strap 1 comprising a fixing element 11, for example, a protrusion, which is introduced into one of the holes 9 made on the strap 1 located close to the end provided with the eyelet 12.

As shown in FIGS. 1-3, the refill 2 has an outer surface 21, an opposite inner surface 22 and a perimeter rim 5 extending around the outer surface 21 and the inner surface 22 and separating the outer surface 21 from the inner surface 22. What is meant by "outer" is the definition of the word as situated on or toward the outside, the exterior. What is meant by "inner" is the definition of the word as situated within or farther within, the interior. What is meant by "perimeter" is the definition of the word as the border or outer boundary of a two-dimensional figure. As represented in FIG. 3, the inner surface 22 is directed toward and lays adjacent the strap 1. The opposite outer surface 21 is on an opposite side of the refill 2 from the inner surface 22 and is not covered and exposed in usage. The perimeter rim 5 extends around both the inner surface 22 and the outer surface 21 and separates the inner surface 22 from the outer surface 21.

The refill 2 is also preferably made of a plastic material, for example, ethylene-vinyl acetate (EVA), and is placed in a housing made in a position substantially centered in the strap 1. To make the placement thereof easier, the inner surface 22 of the refill 2, i.e., the surface in contact with the strap 1 or with the user's wrist in the usage position thereof, is smooth. As shown in FIG. 3, the inner surface 22 is directed toward and lays adjacent the strap 1. The opposite outer surface 21 is on an opposite side of the refill 2 from the inner surface 22 and is directed away from the strap 1 and is exposed and not covered.

For the detachable fixing to the strap 1, the refill 2 comprises a perimetral rim or perimeter rim 5 that abuts with a flange 6 of the strap 1, as can be seen in FIG. 3. Furthermore, the detachable fixing is also performed by means of a protrusion 8 housed inside a securing hole 7 centrally located in the refill 2. The refill 2 can therefore be placed and removed in a simpler manner.

The refill 2 is introduced into a housing 10 of the strap 1 taking advantage of the elastomeric nature of said strap 1, in other words, with the circumferential walls of the housing 10 deforming elastically. To achieve the foregoing, the material of the strap 1 has a Shore A hardness of preferably between 50 and 80, and more preferably of 70.

To increase the evaporation surface of the refill 2, said refill 2 comprises on its outer surface 21, i.e., the surface that is not covered and is exposed to the outside in its usage position, at least one rib 3, defining at least one evaporation chamber 4. What is meant by "rib" is the definition of the word as a vertical ridge.

It must be indicated that, in the depicted embodiment the refill 2 comprises two ribs 3, defining two evaporation chambers 4 that are concentric to one another and an additional evaporation chamber 4 with the perimetral rib 5. However, it is obvious that the refill 2 may comprise any suitable number of ribs 3 and evaporation chambers 4.

According to the depicted embodiment, said ribs 3 define an oval shape when seen in a plan view. However, said ribs 3 may form any suitable shape, for example, a circular, square, or rectangular shape, which may be closed, like in the case of the depicted embodiment, or open.

The evaporation rate is increased with the bracelet according to the present invention as a result of the presence of ribs 3, defining the evaporation chambers 4, such that more volatile substances evaporate from the refill 2 though it is still the same size.

Furthermore, the refill can be placed and removed in a very simple and reliable manner since it has a double retention, on one hand by means of the perimeter rim 5 and the flange 6, and on the other hand by means of the securing hole 7 and the protrusion 8.

Although reference has been made to a specific embodiment of the invention, it is obvious for one skilled in the art that the bracelet described is susceptible to a number of variations and modifications, and that all the mentioned details can be replaced with other technically equivalent details without departing from the scope of protection defined by the attached claims.

The invention claimed is:

1. A bracelet for the diffusion of volatile substances, comprising a strap (1) and a refill (2) impregnated with volatile substances, wherein the refill (2) comprises an inner surface (22) that is directed toward and lays adjacent the strap (1) and an opposite outer surface (21) that is on an opposite side of the refill (2) from the inner surface (22) and is not covered and is exposed in usage, a perimeter rim (5) extending around the inner surface (22) and the outer surface (21) and separating the inner surface (22) from the outer surface (21), and the refill (2) is provided with at least one rib (3) on the outer surface (21) increasing an evaporation surface of the outer surface (21) without increasing a size of the perimeter rim (5) of the refill (2), the at least one rib (3) defining at least one evaporation chamber (4).

2. A bracelet for the diffusion of volatile substances according to claim 1, wherein the outer surface (21) of the refill (2) comprises at least two ribs (3), defining two concentric evaporation chambers (4).

3. A bracelet for the diffusion of volatile substances according to claim 1, wherein the at least one rib (3) defines a circular or oval shape.

4. A bracelet for the diffusion of volatile substances according to claim 1, wherein the outer surface (21) of the refill (2) also comprises a perimeter rim (5) for the detachable fixing of a refill (2) to the strap (1).

5. A bracelet for the diffusion of volatile substances according to claim 4, wherein the strap (1) comprises a flange (6) contacting the perimeter rim (5) for detachably fixing the refill (2) to the strap (1).

6. A bracelet for the diffusion of volatile substances according to claim 1, wherein the refill (2) also comprises a substantially smooth inner surface (22) which, in its usage position, is in contact with the strap (1) or with the user.

7. A bracelet for the diffusion of volatile substances according to claim 1, wherein the refill (2) comprises a securing hole (7) which houses therein a protrusion (8) of the strap (1) in the usage position of the refill (2).

8. A bracelet for the diffusion of volatile substances according to claim 1, wherein the strap (1) is made of an elastomeric plastic material with a Shore A hardness of between 50 and 80, so that it deforms for the insertion and removal of the refill (2).

9. A bracelet for the diffusion of volatile substances according to claim 8, wherein the refill (2) is made of ethylene-vinyl acetate.

10. A bracelet for the diffusion of volatile substances according to claim 2, wherein the one or both of the at least two ribs (3) define a circular or oval shape.

11. A bracelet for the diffusion of volatile substances according to claim 1, wherein the refill (2) is housed inside a housing (10) of the strap (1).

12. A bracelet for the diffusion of volatile substances according to claim 2, wherein the refill (2) is housed inside a housing (10) of the strap (1).

13. A bracelet for the diffusion of volatile substances according to claim 3, wherein the refill (2) is housed inside a housing (10) of the strap (1).

14. A bracelet for the diffusion of volatile substances according to claim 4, wherein the refill (2) is housed inside a housing (10) of the strap (1).

15. A bracelet for the diffusion of volatile substances according to claim 5, wherein the refill (2) is housed inside a housing (10) of the strap (1).

16. A bracelet for the diffusion of volatile substances according to claim 6, wherein the refill (2) is housed inside a housing (10) of the strap (1).

17. A bracelet for the diffusion of volatile substances according to claim 7, wherein the refill (2) is housed inside a housing (10) of the strap (1).

18. A bracelet for the diffusion of volatile substances according to claim 8, wherein the refill (2) is housed inside a housing (10) of the strap (1).

19. A bracelet for the diffusion of volatile substances according to claim 9, wherein the refill (2) is housed inside a housing (10) of the strap (1).

20. A bracelet for the diffusion of volatile substances according to claim 10, wherein the refill (2) is housed inside a housing (10) of the strap (1).

* * * * *